(12) United States Patent
Belfadhel et al.

(10) Patent No.: US 8,058,469 B2
(45) Date of Patent: Nov. 15, 2011

(54) METHOD FOR MAKING CARBAMATES, UREAS AND ISOCYANATES

(75) Inventors: Hatem Abdallah Belfadhel, Roosendaal (NL); Hans-Peter Brack, Herrliberg (CH); Ricardo Godoy-Lopez, Terneuzen (NL); Dennis James Patrick Maria Willemse, Standdaarbuiten (NL)

(73) Assignee: Sabic Innovative Plastics IP B.V. (NL)

( * ) Notice: Subject to any disclaimer, the term of this patent is extended or adjusted under 35 U.S.C. 154(b) by 449 days.

(21) Appl. No.: 12/347,131

(22) Filed: Dec. 31, 2008

(65) Prior Publication Data

US 2010/0113819 A1      May 6, 2010

Related U.S. Application Data

(60) Provisional application No. 61/110,863, filed on Nov. 3, 2008.

(51) Int. Cl.
*C07C 261/00* (2006.01)
*C07C 275/00* (2006.01)
(52) U.S. Cl. ............ 560/132; 560/133; 564/48; 564/63
(58) Field of Classification Search .................. None
See application file for complete search history.

(56) References Cited

U.S. PATENT DOCUMENTS

| | | |
|---|---|---|
| 3,681,457 A | 8/1972 | Babad |
| 3,723,432 A | 3/1973 | Ott |
| 3,759,920 A | 9/1973 | Linder et al. |
| 3,763,217 A | 10/1973 | Brill et al. |
| 3,937,705 A | 2/1976 | Hardtmann |
| 3,937,708 A | 2/1976 | Mentrup et al. |
| 4,086,246 A | 4/1978 | Toth et al. |
| 4,272,441 A | 6/1981 | Keay et al. |
| 4,323,668 A | 4/1982 | Brunelle |
| 4,387,223 A | 6/1983 | Yamamoto et al. |
| 4,474,978 A | 10/1984 | Drent et al. |
| 4,537,960 A | 8/1985 | Merger et al. |
| 4,550,188 A | 10/1985 | Frulla et al. |
| 4,551,169 A | 11/1985 | Takematsu et al. |
| 4,567,287 A | 1/1986 | Frulla et al. |
| 4,725,980 A | 2/1988 | Barcelo et al. |
| 5,463,109 A | 10/1995 | Nishihira et al. |
| 5,962,721 A | 10/1999 | Kim et al. |
| 6,133,473 A | 10/2000 | Berrier |
| 6,420,512 B1 | 7/2002 | McCloskey et al. |

(Continued)

FOREIGN PATENT DOCUMENTS

EP       0065025 A1    11/1982

(Continued)

OTHER PUBLICATIONS

Evans et al., Asymmetric Synthesis of the Enkephalinase Inhibitor Thiorphan, J. Org. Chem,, 1985, pp. 1830-1835, vol. 50(11).

(Continued)

*Primary Examiner* — Karl J Puttlitz
(74) *Attorney, Agent, or Firm* — Cantor Colburn LLP

(57) ABSTRACT

The present invention provides methods of forming carbamates, ureas, and isocyanates. In certain embodiments these methods include the step of reacting an amine with an ester-substituted diaryl carbonate to form an activated carbamate which can be further derivitized to form non-activated carbamate or a urea. The urea or carbamate can be subjected to a pyrolysis reaction to form isocyanate.

18 Claims, 12 Drawing Sheets

U.S. PATENT DOCUMENTS

| | | |
|---|---|---|
| 6,506,871 B1 | 1/2003 | Silvi et al. |
| 6,518,391 B1 | 2/2003 | McCloskey et al. |
| 6,548,623 B2 | 4/2003 | Brunelle et al. |
| 6,790,929 B2 | 9/2004 | Silvi et al. |
| 2003/0100598 A1 | 5/2003 | Mourelle Mancini et al. |
| 2003/0139529 A1 | 7/2003 | O'Neil et al. |
| 2003/0149223 A1 | 8/2003 | McCloskey et al. |
| 2005/0222450 A1 | 10/2005 | Gupte et al. |
| 2007/0270605 A1 | 11/2007 | Srinivas et al. |
| 2007/0282091 A1 | 12/2007 | Buckley et al. |
| 2008/0287640 A1 | 11/2008 | Belfadhel et al. |

FOREIGN PATENT DOCUMENTS

| | | | |
|---|---|---|---|
| EP | 0065026 A1 | | 11/1982 |
| EP | 0083764 B1 | | 7/1983 |
| EP | 0086281 A1 | | 8/1983 |
| EP | 0190466 A1 | | 8/1986 |
| EP | 0296686 A1 | | 12/1988 |
| EP | 1491535 A1 | | 12/2004 |
| JP | 9-143144 | * | 6/1997 |
| WO | 9855450 | | 12/1998 |
| WO | 2005009978 A1 | | 2/2005 |
| WO | 2006000845 A1 | | 1/2006 |
| WO | 2009155592 A1 | | 12/2009 |

OTHER PUBLICATIONS

Fujita et al., Synthesis of 1,3-dialkylurea from ethylene carbonate and amine using calcium oxide, Journal of Molecular Catalysis A: Chemical, Apr. 6, 2005, pp. 43-48, vol. 230.

Majer et al., A Safe and Efficient Method for Preparation of N,N'-Unsymmetrically Disubstituted Ureas Utilizing Triphosgene, The Journal of Organic Chemistry, 1994, pp. 1937-1938, vol. 59(7).

Peng et al., N,N'-phosgenation with triphosgene in the synthesis of direct dyes containing the ureylene group, Dyes and Pigments, Dec. 1996, pp. 193-198, vol. 32, No. 4.

Vauthey et al., An environmentally benign access to carbamates and ureas, Tetrahedron Letters, Aug. 12, 2000, pp. 6347-6350, vol. 41, Issue 33.

Curini et al., Carbamate synthesis from amines and dimethyl carbonate under ytterbium triflate catalysis, Tetrahedron Letters, Jul. 8, 2002, pp. 4895-4897, vol. 43.

* cited by examiner

Urea Preparation
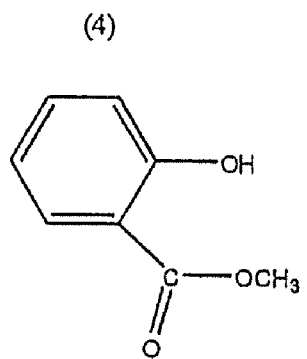
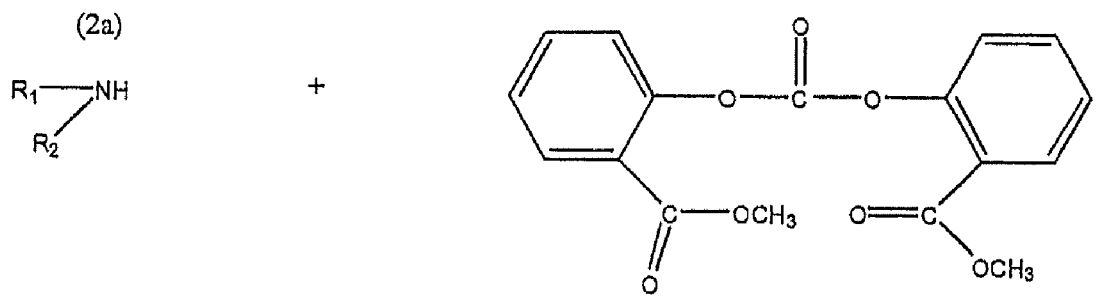
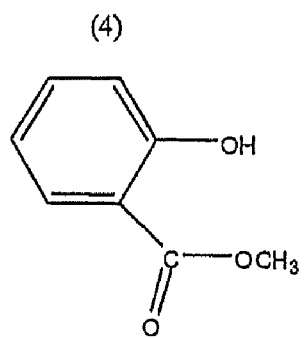
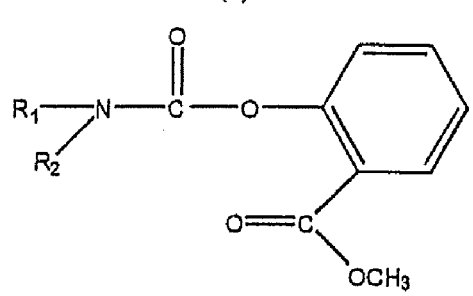
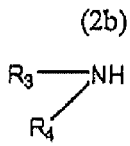
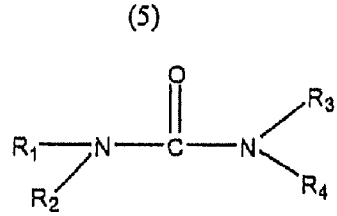
Fig. 2

Fig. 8

| Name (Trade name) | Structure | Applications |
|---|---|---|
| Mephenoxane (Tripedone®) | 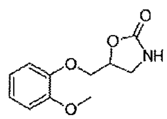 | Skeletal muscle relaxant and anxiolytic. |
| Metaloxane (Skelatin®) | 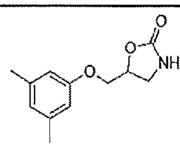 | Skeletal muscle relaxant. |
| Eperozolid (Zyvox™) | 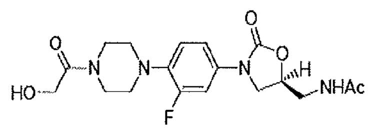 | Antibacterial agent. |
| Lynezolyd (Zyvox™) | 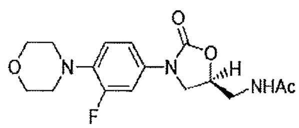 | Antibacterial agent. |
| Fenspiride (Pneumorel) | 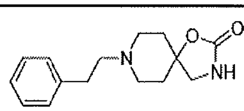 | Treatment of certain respiratory diseases (bronchodilator). |
| Furazolidone (Furoxone) | 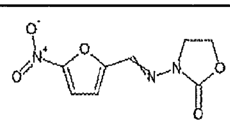 | Antibiotic used to treat diarrhea and enteritis caused by bacteria or protozoan infections |

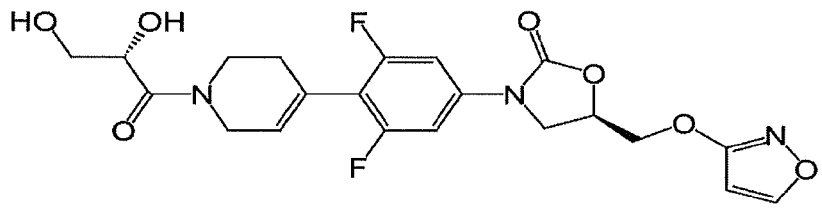

Chemical structure of AZD2563 (AstraZeneca Antibiotic)

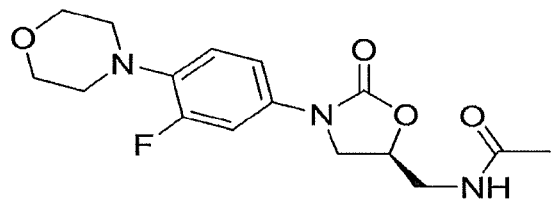

Linezolid (Tradename Zyvoxid®, Pfizer) an Antibiotic
(http://de.wikipedia.org/wiki/Linezolid)

Fig. 9
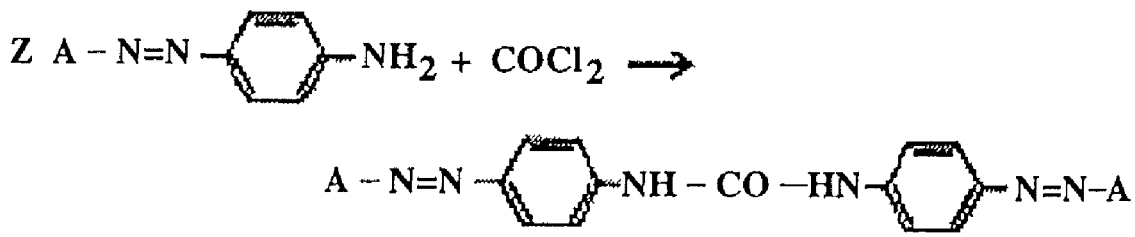
A = azo dye radicals
symetrical
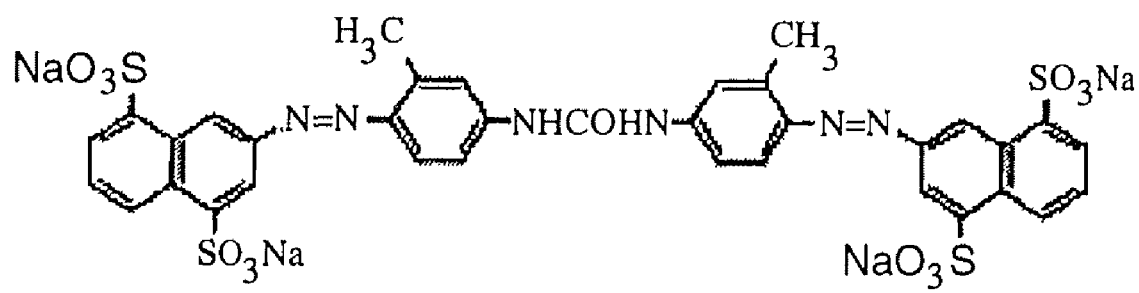
B = azo dye radical
asymetrical
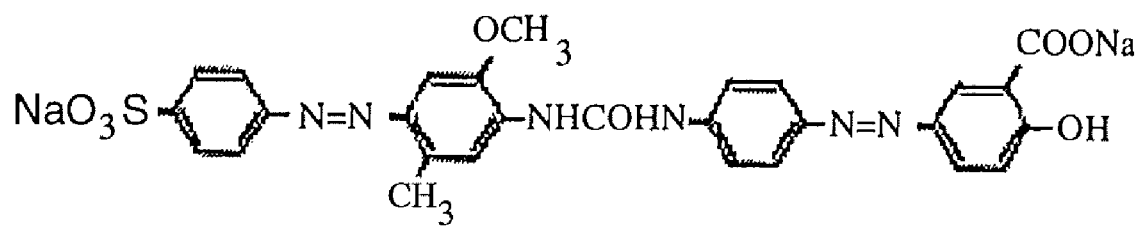

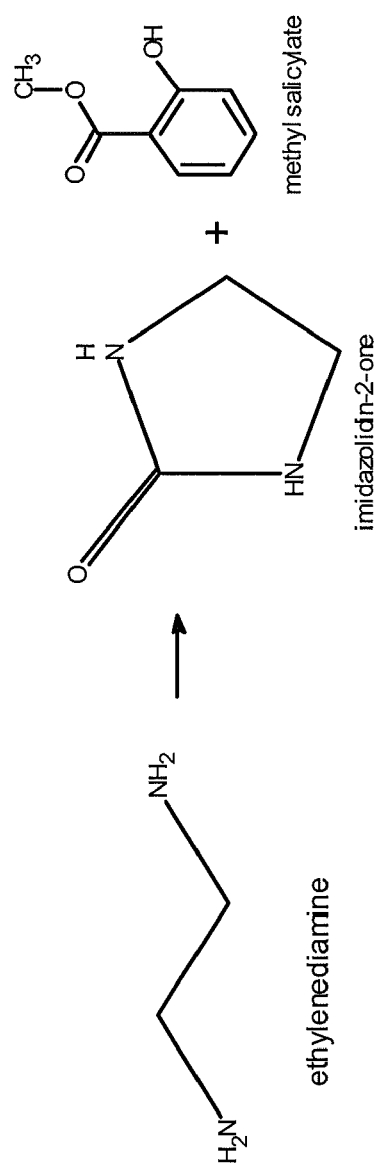
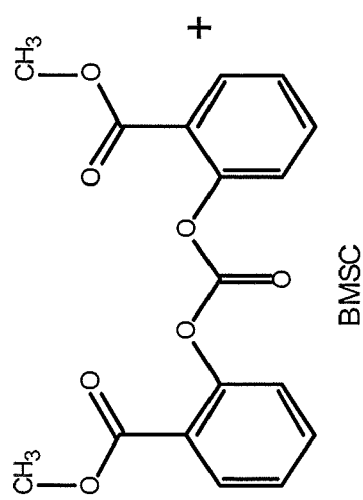
Figure 12

METHOD FOR MAKING CARBAMATES, UREAS AND ISOCYANATES

RELATED APPLICATIONS

The present application is a non-provisional application of U.S. Provisional Patent Application Ser. No. 61/110,863 filed on Nov. 3, 2008, which is incorporated herein by reference for all purposes.

BACKGROUND OF THE INVENTION

This application relates to the preparation of carbamates, ureas, and isocyanates using an activated ester carbonates (e.g. an ester-substituted diaryl carbonate) such as bismethylsalicylcarbonate (BMSC) as a reactant.

Monomeric carbamates, ureas, and isocyanates find substantial utility in a wide variety of applications including fine and specialty chemicals, pharmaceuticals, cosmetics, and agriculture and crop protection. Carbamates and ureas share a common structural element in which a carbonyl group is flanked by an oxygen and a nitrogen (carbamates) or two nitrogens (ureas). Isocyanates can be made by pyrolysis of a carbamate or a urea.

Commonly, carbamates and ureas are synthesized by reactions making use of phosgene gas or a solid phosgene precursor such as triphosgene in a reaction with two amines or an amine and an alcohol. The adoption of triphosgene is preferred for safety reasons, even though it costs more and is generally less reactive, requiring longer reactions at higher temperatures. However, triphosgene is only "safe" relative to phosgene itself and it is still classified as a very hazardous material that can generate hazardous decomposition products namely hydrogen chloride, chlorine, phosgene in addition to the carbon monoxide as well as carbon dioxide normally resulting from the extreme thermal degradation of organic compounds. Carbamates (also known as urethanes) can also be made from reaction of a urea intermediate with an alcohol. Dimethyl carbonate and diphenyl carbonate are also used for making carbamates and ureas, but they require long reactions times and/or high temperatures, and/or catalyst to achieve this result.

SUMMARY OF THE INVENTION

The present invention provides a method for the synthesis of monomeric carbamates and ureas through the reaction of alcohol and/or amine precursors with an ester-substituted diaryl carbonate, such as BMSC. The reaction can be carried out at low temperatures, for example at room temperature, to provide high yields of the product in relatively short period of time. Furthermore, the breakdown products of BMSC are methyl salicylate and salicylic acid, both of which at low concentrations are accepted ingredients in foods and pharmaceuticals.

Thus, in accordance with the invention there is provided a compound and a method of making a compound of the formula:

$$X_1-C(=O)-X_2$$

wherein $X_1$ is $NR_1R_2$ and $X_2$ is $NR_3R_4$ or $OR_5$, and wherein $R_1$, $R_2$, and $R_3$ and $R_4$, if present, are each independently selected from the group consisting of hydrogen, optionally-substituted linear or branched alkyl, alkene, cycloalkyl, cycloalkenyl, aryl, heteroatom-containing aryl, and aralkyl groups, or $R_1$ and $R_2$ in combination are a carbon atom double bonded to the nitrogen of $X_1$ or $R_3$ and $R_4$ in combination are a carbon atom double bonded to the nitrogen of $X_2$ or the N of $X_1$ or $X_2$ may be the nitrogen of a ring system, and $R_5$, if present, is selected from the group consisting of optionally-substituted linear or branched alkyl, aryl, and aralkyl groups, or $R_1$ or $R_2$ in combination with $R_3$, $R_4$, or $R_5$ form a five or six-member ring, said method comprising reacting $HNR_1R_2$, and $HNR_3R_4$ or $HOR_5$ with an ester-substituted diaryl carbonate to form the compound. The optional substituents may each independently be chemical functional groups that are not reactive under the transesterification conditions used to prepare the further derivatized carbamate species. Such optional substituents include halogen, vinyl, carbonyl, ether, cycloether, azo, sulfide/thio, alcohol, and heterocyclics substituents. In specific embodiments, the ester-substituted diaryl carbonate is BMSC. In a further embodiment, the compound may be subjected to a pyrolysis reaction to form an isocyanate.

In another embodiment, the present invention provides a carbamate of the formula:

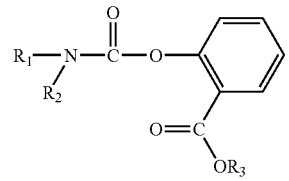

wherein $R_1$, and $R_2$ are each independently selected from the group consisting of hydrogen, optionally-substituted linear or branched alkyl, alkene, cycloalkyl, cycloalkenyl, aryl, heteroatom-containing aryl, and aralkyl groups, or $R_1$ and $R_2$ in combination are a carbon atom double bonded to the nitrogen or $R_1$ and $R_2$ are members of 5 or 6 membered ring, and $R_3$ is alkyl, aryl, or aralkyl.

BRIEF DESCRIPTION OF THE DRAWINGS

FIG. 2 shows a reaction scheme for the preparation of ureas in accordance with the invention.

FIGS. 7 and 8 show structures of exemplary compounds of commercial interest having a carbamate functional group or its derivative.

FIG. 9 shows exemplary structures of aminoazo dyes that can be made using the method of the invention.

FIG. 12 shows a cyclic urea formation reaction in accordance with the example section.

DETAILED DESCRIPTION OF THE INVENTION

Figure 1A:
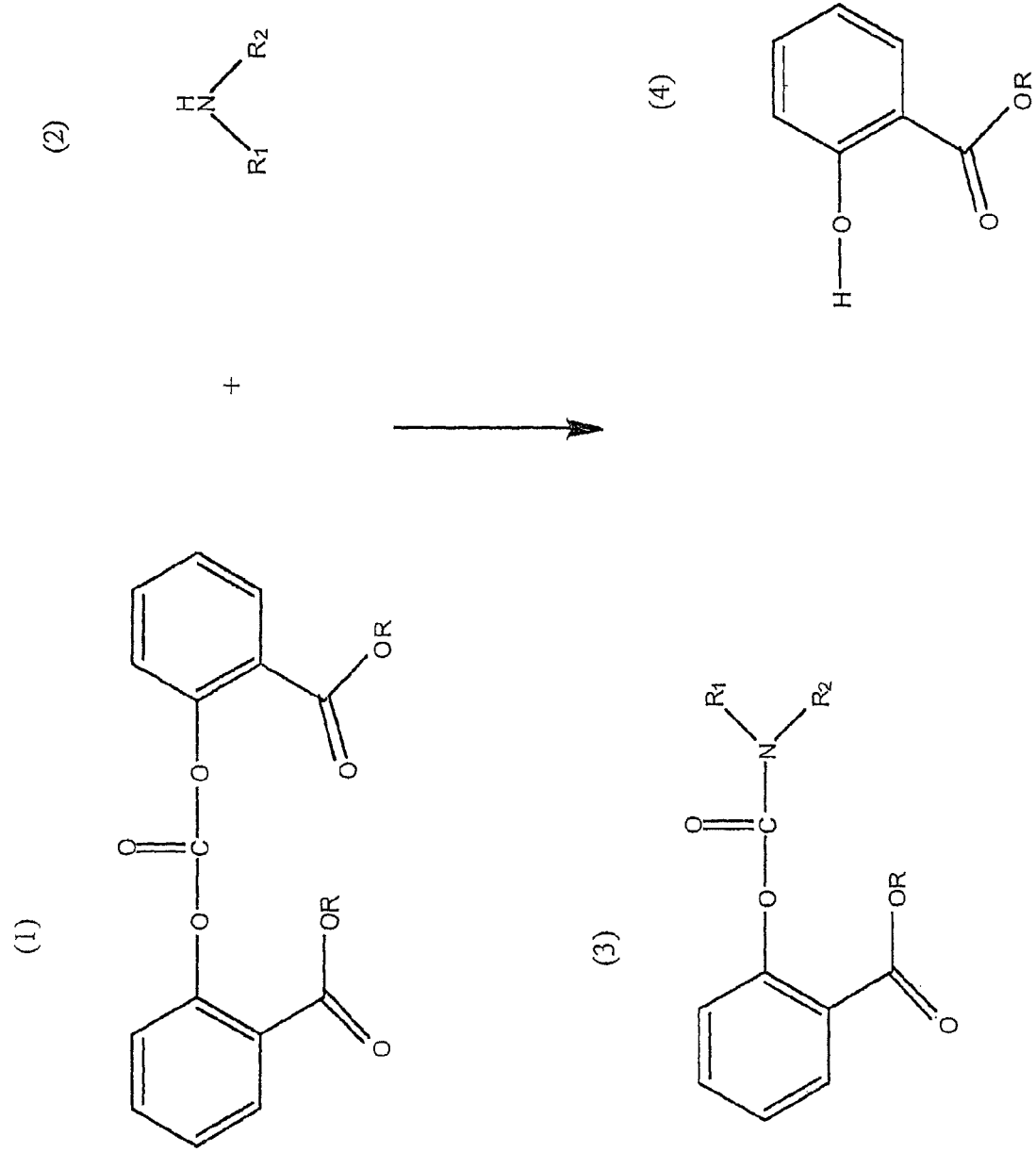
FIGS. 1A and B show reaction schemes for the preparation of carbamates in accordance with the invention.

The present invention provides a powerful synthetic method for the synthesis of carbamates and ureas per se or as intermediates in the synthesis of isocyanates. The invention is of general applicability for reactions with primary or secondary amines alone or in combination with primary or secondary alcohols, and for reactions with diamines and amino alcohols for the formation of ring structures containing the urea or carbamate functional group. The compounds may be further reacted to form derivative compounds, including isocyanates, and sulfur containing compounds.

Definitions

"carbamate" refers to a class of chemical compounds sharing the same functional group RR'N—CO—OR" based on a carbonyl group flanked by an organic alcohol and an organic amine residues. The R groups on the amine and the alcohol residue may form a ring.

"urea" refers to a class of chemical compounds sharing the same functional group RR'N—CO—NR"R'" based on a carbonyl group flanked by two organic amine residues. The R groups on the amine residues may form a ring.

"monomeric carbamates and ureas" refers to compounds in which the carbamate or urea function group does not form a repeating unit in a polymer chain. Where an amine or alcohol reactant is monofunctional, polymerization cannot occur. In the case where a reactant is difunctional such that polymerization could occur, this term refers to the portion of the product that is a non-polymer product.

"ester-substituted diaryl carbonates" refers to compounds of the general formula

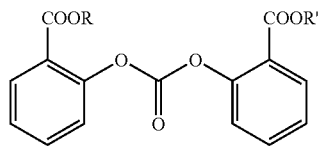

in which R and R' are individually alkyl, for example, methyl, ethyl, or propyl, aryl for example phneyl, or aralkyl, for example benzyl. A preferred ester-substituted diaryl carbonate is bismethylsalicylcarbonate (R═R'═methyl). (Ortho-alkoxycarbonylaryl)carbonates of this type are known for use in the preparation of polycarbonates, for example from U.S. Pats. Nos. 4,323,668; 6,420,512; 6,506,871; 6,548,623, 6,790,929, 6,518,391, and US Patent Publications US 2003/0139529 and US 2003/0149223, all of which are incorporated herein by reference. Methods for making ster-substituted diaryl carbonates are described in US Patent Publication No. 2007/0282091 which is incorporated herein by reference.

Reference throughout the specification to "one embodiment," "another embodiment," "an embodiment," "some embodiments," and so forth, means that a particular element (e.g., feature, structure, property, and/or characteristic) described in connection with the embodiment is included in at least one embodiment described herein, and may or may not be present in other embodiments. In addition, it is to be understood that the described element(s) may be combined in any suitable manner in the various embodiments.

Numerical values in the specification and claims of this application reflect average values for a composition. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

Carbamate Synthesis

Figure 1B:
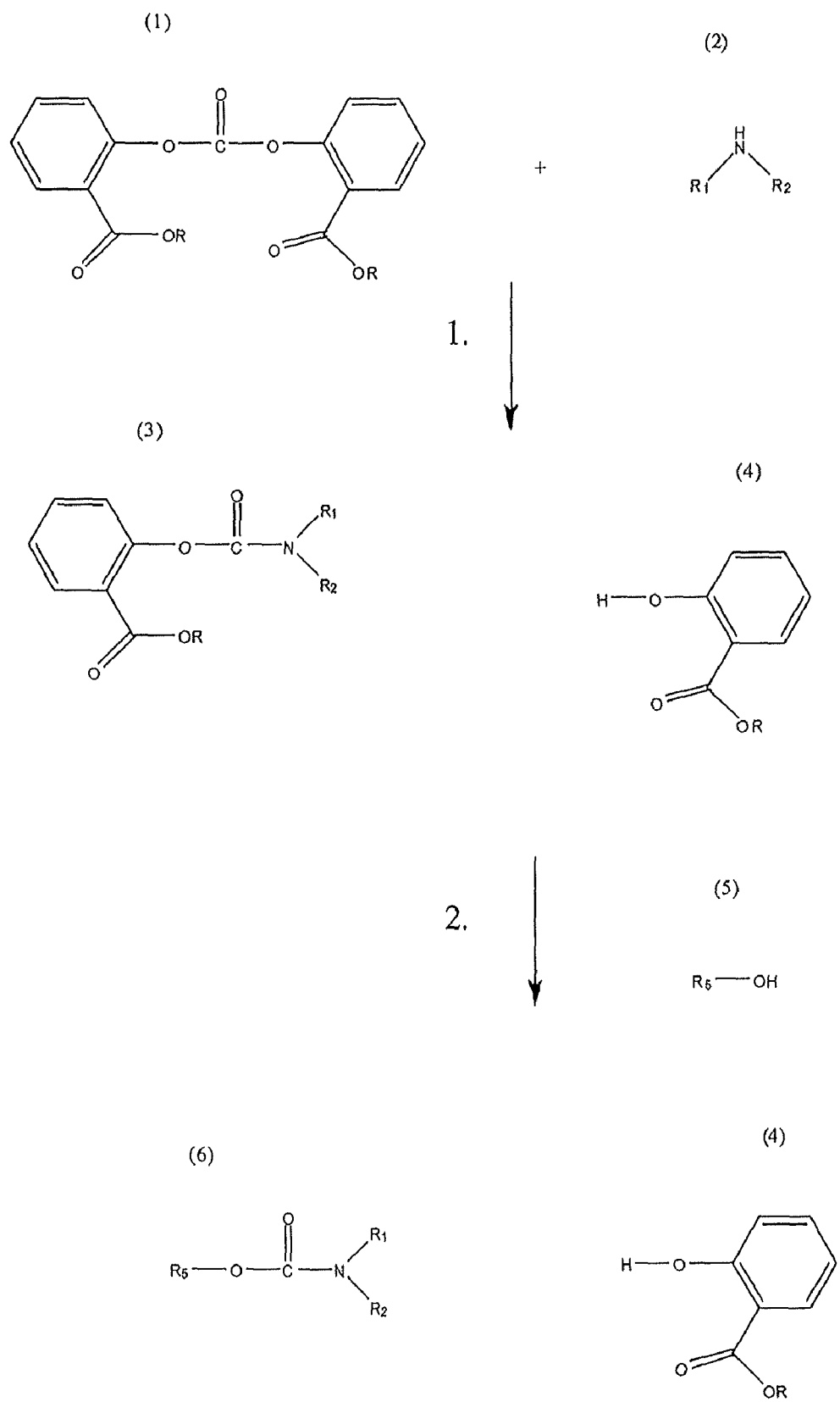

The general preparation scheme for the synthesis of carbamates in accordance with the invention is shown in FIGS. 1A and 1B. Ester-substituted diaryl carbonates (1) are reacted together with optionally functionalized primary and secondary amines (2). The reaction yields an activated carbamate species (3) and a phenolic byproduct (4). The activating groups R are each independently an ortho-ester substituent. The ester substituent R may be alkyl, phenyl, or benzyl. The amine substituents $R_1$ and $R_2$ are each independently optionally-substituted linear or branched alkyl, phenyl, aryl or aralkyl groups. The optional substituents may each independently be chemical functional groups that are not reactive under the transesterification conditions used to prepare the further derivitized carbamate species ((6) in FIG. 2). Such optional substituents include halogen, vinyl, and carbonyl substituents. The phenolic byproduct (4) may be recycled to produce additional activated carbonate starting material, for example, by the phosgenation of the phenolic compound.

In this reaction, specific amine reactants and reactions conditions are selected in combination to arrive at the desired product. The reactions of amines with BMSC go essentially to full conversion even at relatively low reaction temperatures, e.g. room temperature. To make carbamates, it is preferred that the BMSC and the amine are present in a molar ratio (amine:BMSC) of 1:1 or less since higher ratios will tend to lead to formation of ureas. However, mole ratios (amine:BMSC) of greater than 0.90:1, for example 0.95:1 can be used.

The reaction to form carbamates may be carried out in solution using inert solvents such as dichloromethane, chloroform, or acetonitrile, interfacially, or in the melt. Suitable reaction temperatures will typically be high enough to keep the solution or melt in the liquid form and not high enough to cause loss of the species 1, 2, 3, 5, or 6 in FIGS. 1 and/or 2. The reaction temperature is less than 120° C., preferably less than 100° C., more preferably less than 60° C. Higher reaction temperatures may be appropriate when more sterically hindered amines are used as reactants if longer reaction times are not acceptable.

In one embodiment, the reaction temperature may be selected such that product species 3 and 6 are devolatized to separate these reaction products from reactants and byproducts and to drive the reaction toward full conversion. In another embodiment the reaction temperature is selected such that byproduct 4 is devolatized to separate this reaction byproduct from the products. In a further embodiment, the reaction temperature is selected so that product species 3 and 6 and byproduct 4 are devolatized from the non-reacted reactants and later separated. Such a devolatization/reaction temperature schemes of the reaction products could be employed to help favor full conversion and make it easier to run the process continuously or semi-continuously (e.g. continuous feed of the reactants and devolatization of the reaction products). Adding a distillation column could also allow a proper separation of the components. However, it is important to note that more undesired side reactions and byproducts are observed at elevated reaction temperatures (e.g. at temperatures above about 150° C., especially above about 200° C.).

Water may optionally be present during the reaction, but it is important to limit the amount of water present because ortho-substituted diaryl carbonates such as BMSC are readily hydrolyzed to methyl salicylate and even salicylic acid in the presence of basic compounds such as amines and water, especially at elevated temperatures, see for example, U.S. patent application Ser. No. 11/748,951, which is incorporated herein by reference. Therefore the amount of water present should be less than 1 mole %, preferably less than 100 ppm, more preferably less 10 ppm, and most preferably less than 1 ppm based on the concentration of the ortho-ester-substituted diaryl carbonate. In one embodiment, water is essentially absent during the reaction of the ortho-ester-substituted carbonate.

Reaction times may be 72 hours or less, preferably 24 hours or less, more preferably 12 hours or less, most preferably 4 hours or less. In some embodiments, the reaction time may be as little as 1 hour or less, preferably 30 min or less. Longer reaction times may be appropriate when more sterically hindered amines are used as reactants.

Catalysts may optionally be used to increase the reaction rate, and suitable catalysts include transesterification catalysts, inorganic and organic bases, and metal oxide catalysts such as CaO, ZnO, MgO, $ZrO_2$, and $Al_2O_3$. In one embodiment, no catalyst is added. The use of optional catalysts may be preferable when more sterically hindered amines are used as reactants to maintain shorter reaction times and lower reaction temperatures.

Suitable amine reactants for use in the formation of carbamates are compounds of the formula $HNR_1R_2$, wherein $R_1$, and $R_2$ are independently hydrogen, optionally-substituted linear or branched alkyl, alkene, cycloalkyl, cycloalkenyl, aryl, heteroatom-containing aryl, and aralkyl groups, or $R_1$ and $R_2$ in combination are a carbon atom double bonded to the nitrogen of $X_1$, or the N of $X_1$ or $X_2$ may be the nitrogen of a ring system such as piperidine, pyrrolidine, morpholine, piperazine, or 2-pyrrolidone, or a 2-imadazolyl or pyrazolyl substituent.

As shown in FIG. 1B, the methylsalicyl carbamate (e.g. activated carbamate species (3)) of the invention may be further reacted with alcoholic and phenolic compounds (e.g. $R_5$—OH (5)) to yield a further substituted carbamate compound (6) in which the methylsalicyl group is replaced by $R_5O$—. $R_5$ is a suitably optionally-substituted:

linear or branched alkyl, such a methyl, ethyl, n-propyl, iso-propyl, n-butyl and iso-butyl aryl, for example phenyl, tolyl or xylyl, or aralkyl groups such as benzyl. Catalysts can be used to increase the reaction rate when alcohol reactants (e.g. $R_5$—OH) are used, and suitable catalysts include transesterification catalysts, inorganic and organic bases such as NaOH, and metal oxide catalysts such as CaO, ZnO, MgO, $ZrO_2$, and $Al_2O_3$.

Cyclic carbamates such as 2-oxazolidones are formed from the reaction of the ester-substituted diaryl carbonate with an amino alcohol. Suitable amino alcohols have the general formula:

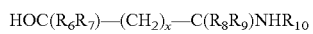

$HOC(R_6R_7)$—$(CH_2)_x$—$C(R_8R_9)NHR_{10}$ in which x is 0 or 1 and $R_6$, $R_7$, $R_8$, $R_9$ and $R_{10}$ are independently selected from the group consisting of hydrogen, linear or branched alkyl, such a methyl, ethyl, n-propyl, iso-propyl, n-butyl and iso-butyl aryl, for example phenyl, or aralkyl groups such as benzyl. When x=0, the substituents $R_6$, $R_7$, $R_8$, $R_9$ can also form a saturated or unsaturated ring. For example, the amino alcohol could be 2-amino cyclohexanol, or 2-aminophenol, in which case the reaction results in a compound with two rings. 2-oxazolidones with varying substituents on the ring (phenyl and methyl; phenyl; and benzyl) are used as Evan's chiral auxiliaries, for example, see Evans and Mathre, *J. Org. Chem.* Vol. 50 (1985) p. 1830-1835.

The amine, alcohol and ester-substituted reactants are preferably selected such that each has a molecular weight of no more than 3000 daltons, preferably no more than 2000 daltons, and most preferably no more than 1000 daltons.

Figure 7:
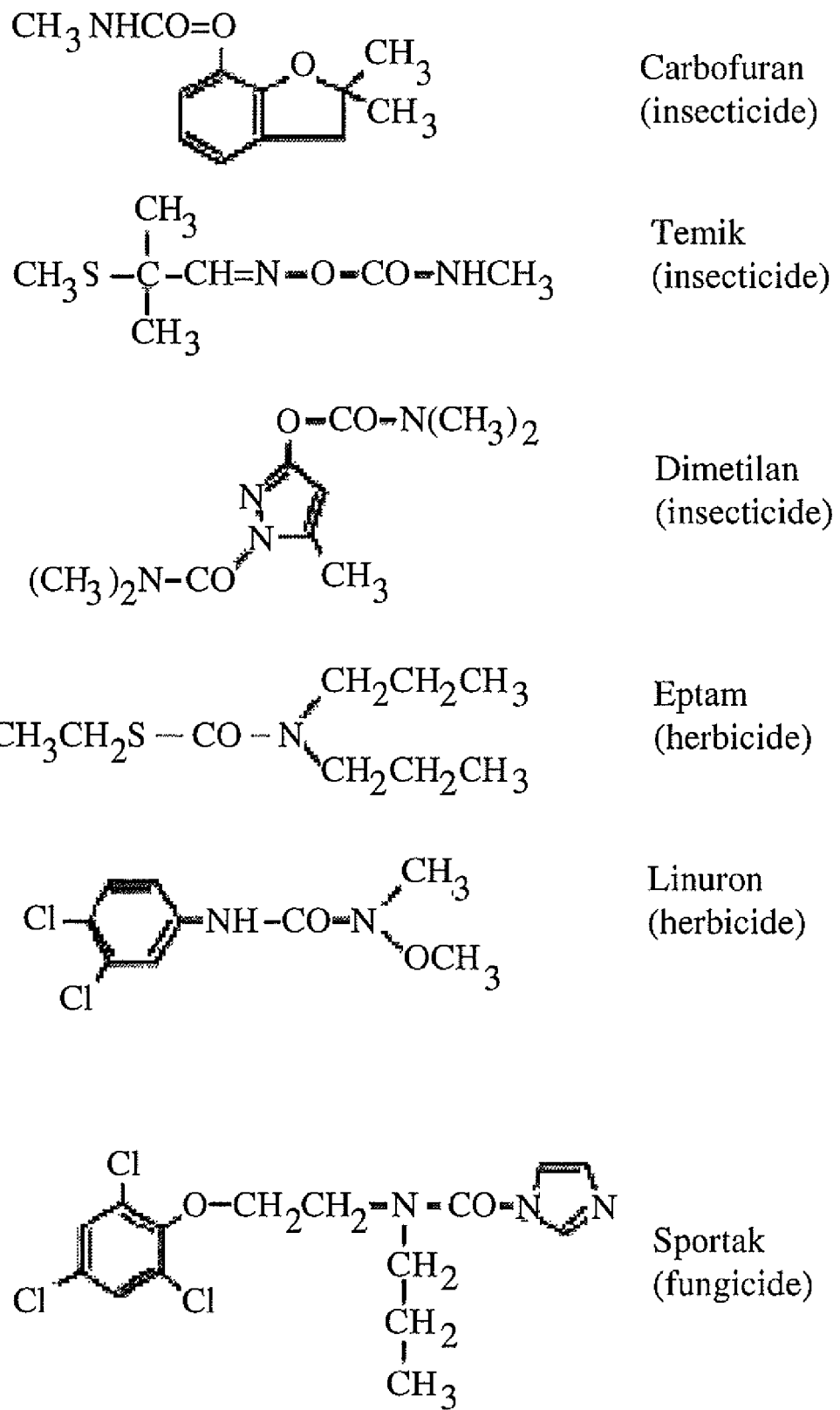

Carbamate functional group are found in insecticides, for example, Aldicarb (CAS #116-06-3), Carbofuran (CAS#1563-66-2) marketed under the trade name Furodan by FMC Corp., Fenoxycarb (CAS#72490-01-8), Carbaryl (CAS #63-25-2) marketed under the trade name SEVIN by Bayer Corp., Ethienocarb (CAS #58270-08-9), and 2-(1-Methylpropyl)phenyl N-methylcarbamate. In addition, the cholinesterase inhibitors neostigmine and rivastigmine have carbamate functionality. Other examples of commercially important carbamate compounds are meprobamate and its derivatives, a class of anxiolytic drugs. The insect repellent icaridin (hydroxyethyl isobutyl piperidine carboxylate) is a substituted carbamate. Structures of exemplary compounds of commercial interest with or derivable from a carbamate are shown in FIG. 7 and FIG. 8.

Urea Synthesis

Reaction of the ester-substituted diaryl carbonate (1) with the amine species (2) (or alternatively two different amines) as shown in FIG. 1 can also be allowed to proceed further to prepare urea compounds. For example, reaction of ester-substituted diaryl carbonate (1) with an excess of amine (molar stoichiometric ratio of total amine compound(s) to ortho-ester-substituted activated carbonate is 1:1 or more) will result in the formation of ureas by further derivitization of the activated carbamate intermediate (3), as shown in FIG. 2. In FIG. 2, the reaction is shown with BMSC specifically, but other ester-substituted diaryl carbonates may also be used. In FIG. 2, the substituents $R_1$-$R_4$ are independently an optionally substituted linear or branched alkyl, phenyl, aryl, or aralkyl. The optional substituents may each independently be chemical functional groups that are not reactive under the transesterification conditions used to prepare the further derivitized carbamate species (5). Such optional substituents include halogen, vinyl, and carbonyl substituents. This preparation of a urea may be carried out in two steps (first activated carbamate synthesis (as in FIG. 1A) followed by urea synthesis), for example, when it is desirable to prepare an asymmetrical urea from two different amines. The phenolic byproduct (4) may again be recycled to produce additional activated carbonate starting material, for example, by the phosgenation of the phenolic compound.

The conditions and considerations for the formation of ureas are generally the same as for carbamates as explained above, except that the molar ratio is greater so that approximately at least two moles (for example 1.9 to 2.2 moles) of amine are present for each mole of ester-substituted diaryl carbonate. This is a molar stoichiometric ratio of at least 1:1 of amine are present for each mole of activated carbamate (3). Suitable reactants are the amine reactants as described above.

Aminoazo dyes are an example of compounds previously prepared by the reaction of amines with phosgene which are effectively prepared using the present invention. FIG. 9 contains exemplary structures of such dyes.

Figure 11:
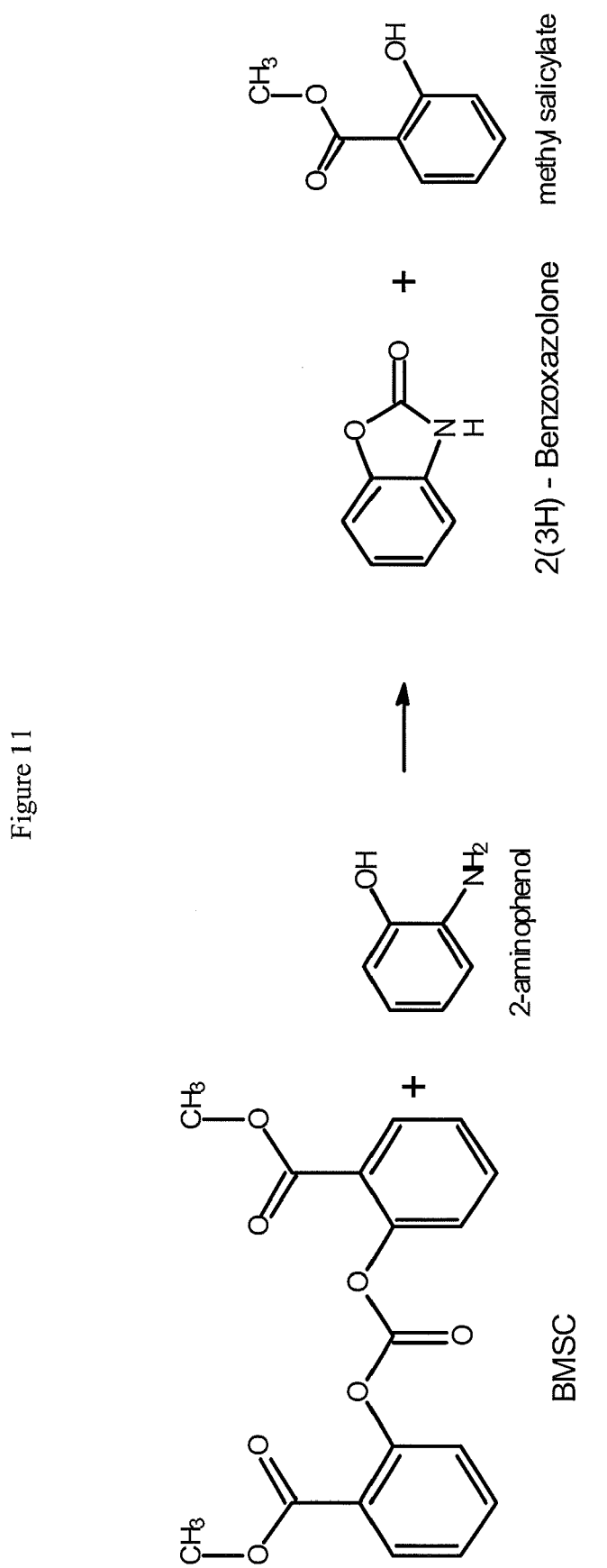
FIG. 11 shows a cyclic carbamate formation reaction in accordance with the example section.

Cyclic ureas such as 2(3H)-Benzoxazolone are formed from the reaction of the ester-substituted diaryl carbonate with a diamine, as shown in FIG. 11. Suitable diamines have the general formula:

$R_{11}HNC(R_6R_7)$—$(CH_2)_x$—$C(R_8R_9)NHR_{10}$ in which x is 0, 1, or 2 and $R_6$, $R_7$, $R_8$, $R_9$ and $R_{10}$ are independently selected from the group consisting of hydrogen, linear or branched alkyl, such a methyl, ethyl, n-propyl, iso-propyl, n-butyl and iso-butyl aryl, for example phenyl, or aralkyl groups such as benzyl. When x=0, the substituents $R_6$, $R_7$, $R_8$, $R_9$ can also form a saturated or partially unsaturated ring. For example, the amino alcohol could be 2-amino cyclohexanol to result in a compound with two rings.

For example, the cyclic urea 1,3-Dimethyl-3,4,5,6-tetrahydro-2(1H)-pyrimidinone (DMPU) which can be used as a polar, aprotic organic solvent could be made by reaction of N,N'-dimethyl-1,3, propanediamine with an ester-substituted diaryl carbonate. Other cyclic ureas of commercial interest include barbituates, allantoin (CAS #97-59-6), hydantoin (CAS #461-72-3), and imidazolidinyl urea (CAS #39236-46-9) (a condensation product of two allantoin's and formaldehyde). Quinazolinone derived cyclic ureas are disclosed in U.S. Pat. Nos. 3,723,432, 3,759,920, 3,937,705 and 4,387,223 which are incorporated herein by reference. Other cyclic ureas are described in U.S. Pat. No. 3,937,708, which is incorporated herein by reference.

Asymmetric ureas can be formed using a stepwise process in which a carbamate is first form with one amine (approximately a 1:1 mole ratio), and then further reacted with a second amine.

Isocyanate Synthesis

Figure 3A:
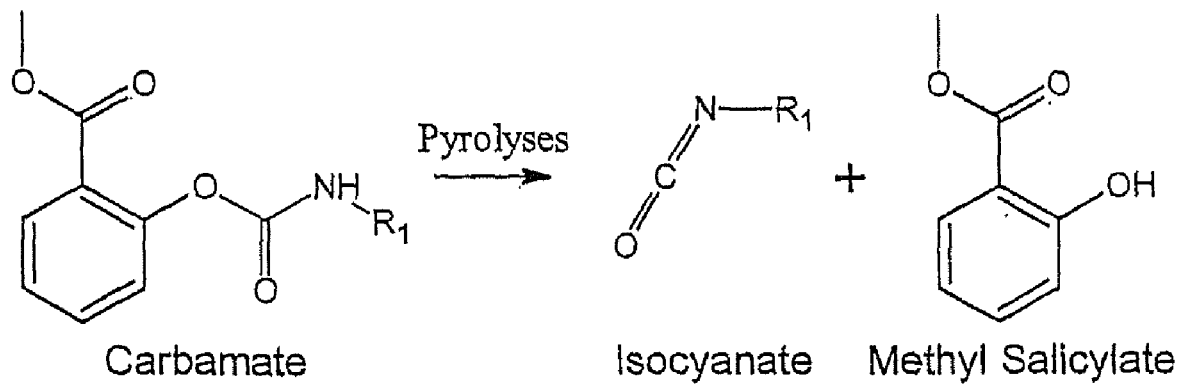
FIGS. 3A and B show the conversion of carbamates and ureas, respectively, to isocyanates.
Figure 3B:
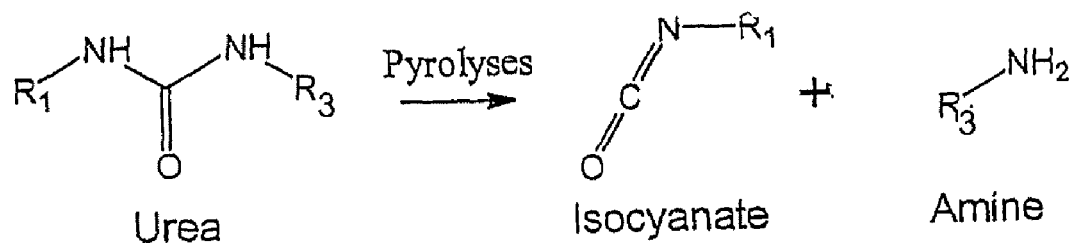

The preparation of isocyanates from carbamates or ureas formed as described above, may be carried out by pyrolysis reactions as shown in FIGS. 3A and B. Pyrolysis is suitably performed at elevated temperatures for example 200-250° C. or greater. In the specific examples below, temperatures of 350° C. were used.

EXAMPLES

Having described the invention in detail, the following examples are provided. The examples should not be considered as limiting the scope of the invention, but merely as illustrative and representative thereof.

(WE) as used herein is understood to mean "working example" while (CE) is understood to mean "comparative example". The terms "working" and "comparative" are simply used to demonstrate comparisons to other examples. Working and comparative examples may or may not be an example within the scope of the present invention.

In the following examples the following processes, measurements, and experimental tests were performed.

Preparation of 1-methylsalicyl-N-diethylcarbamate

Example 1

The reaction was carried out by dissolving 6 grams of BMSC (source: Sabic Innovative Plastics NL) and 1.3 g of DEA (diethyl amine, Sigma-Aldrich, Product reference: 259454-25G, Lot #02819MI, 97%) (molar stoichiometric ratio 1:1) in 18 ml of dichloromethane. The synthesis was carried out in glassware that had been treated in a HCl solution (1M) for 24 hours in order to remove all traces of sodium ions that could be present on the glass surface and act as a catalyst in the reaction. The reaction was simply carried out by mixing the solution for 30 minutes at room temperature.

Example 2

The procedure of Example 1 was repeated, except that a molar stoichiometric ratio of BMSC/DEA equal to 0.95 was used.

Example 3

The procedure of Example 1 was repeated except that a molar stoichiometric ratio of BMSC/DEA equal to 1.05 was used.

GCFID was used to characterize the composition of the unpurified reaction product from Examples 1-3. Samples were diluted (100×) in dichloromethane (GC grade). Diluted sample was then placed in an auto-sampler vial and injected into an Agilent 6890 gas chromatograph under the following instrumental conditions:

Instrumental Settings
Injector
Injection volume: 1 μl
Injection Mode: Split (40:1)
Injector temperature: 225° C.
Oven temperature program
Initial temp: 35° C.
Initial time: 5.00 min
Ramp: 15° C./min, final temp 300° C., ramp time 10 min.
Run Time: 32.67 min.
Column
Type: 100% dimethylpolysiloxane (30.0 m×320.00 μm×0.50 um)
Pressure: 8.30 psi
Nominal initial flow: 2.0 ml/min
Average velocity: 33 cm/sec
Carrier gas: Nitrogen
Detector
Type: Flame ionization
Temperature: 310° C.
The detection limit for the GC-FID method was 0.025%

Calculations

Peaks appearing in the chromatogram were identified by GC-MS experiments. In separate spiking experiments diethyl urea, a potential unwanted byproduct, was found both to be analyzable by the method and to be absent from reaction samples. The relative response factors for BMSC, MS and DEA were determined using injection of external standards of the same concentration and found to be equal within experimental error (approx 3%). Since no external standard was available for the carbamate specifically, its response factor was assumed to be equal to that of the other analytes for calculations. This was confirmed when the pure carbamate was obtained.

The four peaks were integrated and (assuming equal response factors) the individual peak areas were expressed as a percentage of the sum of the total area to give a final indication of the concentration for each component.

The results of this analysis are shown in Table 1.

TABLE 1

Ratio screening for synthesis carbamate.

| Example | Ratio | Area % MS | Area % Carbamate | Area % BMSC | Area % DEA | Area % DEU |
|---|---|---|---|---|---|---|
| 1 | 1:1 | 39.1 | 60.9 | BDL | BDL | BDL |
| 2 | 1:0.95 | 38.3 | 53.6 | 8.1 | BDL | BDL |
| 3 | 1:1.5 | 33.0 | 56.0 | BDL | 11.0 | BDL |

(BDL = Below Detection Limit)

These results show high conversion of reactants in carbamate. In fact, the yield of carbamate in example 1 is nearly quantitative, since nothing but the carbonate and the by-product methyl salicylate was detected.

NMR analysis was performed on a purified product (1-methylsalicyl-N-diethylcarbamate) from Example 1 after passing it through a silica column and distilling off the volatile byproducts on a rotovap set-up. Proton NMR and Carbon NMR analyses were done with the Avance 400 Ultrashield Magnet in 400 MHZ using the setting shown in Table 2.

TABLE 2

NMR Instrumental settings

| Description | $^{13}$C-NMR | $^{1}$H-NMR |
|---|---|---|
| SF | 100 MHz (Avance 400, Ultrashielded Magnet) | 400 MHz (Avance 400, Ultrashielded Magnet) |
| Sweep width | 20 ppm | 16 ppm |
| Number of scans | 512 | 32 |
| Concentration | 5-10 wt % in CDCl$_3$ (Calibration at 77.0 ppm) | 5-10 wt % in CDCl$_3$ |
| Probe head | 5 mm QNP tuned for $^{13}$C frequency | 5 mm QNP |
| Recycle delay | 4 seconds | 10 seconds |
| Decoupling | Waltz 16 | — |
| Plus width | 30° C. | 30° C. |

The spectra were consistent with the formation of the desired product, 1-methylsalicyl-N-diethylcarbamate.

Example 4

The procedure of Example 1 was repeated (molar stoichiometric ratio of BMSC/DEA equal to 1.0) except that a reaction time of 15 minutes was used.

Example 5

The procedure of Example 1 was repeated (molar stoichiometric ratio of BMSC/DEA equal to 1.0) except that a reaction time of 45 minutes was used.

Example 6

The procedure of Example 1 was repeated (molar stoichiometric ratio of BMSC/DEA equal to 1.0) except that a reaction time of 60 minutes was used.

Table 3 shows the results of differences in reaction time based on examples 1 and 4-6.

TABLE 3

Influence of reaction time.

| Example | Time (min) | Ratio | Area % MS | Area % Carbamate | Area % BMSC | Area % DEA | Area % DEU |
|---|---|---|---|---|---|---|---|
| 4 | 15 | 1:1 | 36.1 | 64.4 | BDL | 8.7 | BDL |
| 1 | 30 | 1:1 | 36.5 | 64.1 | BDL | BDL | BDL |
| 5 | 45 | 1:1 | 42.2 | 58.6 | BDL | BDL | BDL |
| 6 | 60 | 1:1 | 38.4 | 62.2 | BDL | BDL | BDL |

(BDL = Below Detection Limit)

Example 7

The procedure of Example 1 was repeated (molar stoichiometric ratio of BMSC/DEA equal to 1.0) except that a reaction time of 12 hours and a reaction temperature of (~7° C.) was used. The results are shown in Table 4.

TABLE 4

Influence of reaction temperature.

| Reaction | Area % MS | Area % DEA | Area % BMSC | Area % Carbamate | Area % DEU |
|---|---|---|---|---|---|
| In refrigerator | 34.4 | BDL | 3.9 | 61.7 | BDL |

(BDL = Below Detection Limit)

Examples 4 to 7 demonstrate that carbamates can be made in essentially full conversion within reaction times as short as 15 min and that BMSC maintains its high reactivity with amines even at sub-ambient temperatures.

Purification of 1-methylsalicyl-N-diethylcarbamate

After the synthesis step a purity of ~60% was typically obtained at a reactant stoichiometric ratio equal to 1, and the carbamate was typically present in a mixture together with the methyl salicylate byproduct, the dichloromethane solvent, and some low levels of unreacted BMSC. In order to obtain the carbamate species in high purity (>99%), several potential purification methods were evaluated. These methods included distillation, rotovapping, rotovapping followed by silica column treatment, or silica column treatment followed by rotovapping. These methods are summarized in the following examples.

Example 8

A batch vacuum distillation of a scaled-up reaction product as prepared in Example 1 was done by building a vacuum distillation set-up and removing the solvent (dichloromethane) and the byproduct (methyl salicylate) in two steps due to the large difference in their boiling points. For example, the atmospheric boiling point of dichloromethane is 40° C., and that of methyl salicylate is 222° C. After this distillation process a sample was taken and analyzed for its purity. The purity after batch vacuum distillation was however only ~78%, and the major impurities were MS and BMSC.

Example 9

Another portion of the same unpurified reaction product from Example 8 was taken and purified as follows. Rotavap was done in a similar way as the batch vacuum distillation, the only difference was that the rotavap is a fixed set-up and therefore easier to use. The distillation steps are identical to the batch vacuum distillation. After rotovapping, a sample was taken and analyzed for its purity. The purity after batch vacuum distillation was only ~62%, and the major impurities were again MS and BMSC.

Example 10

A portion of the purified reaction product (solution) from the rotovap treatment in Example 9 was taken and further purified by running it through a silica column. The column was made by slurrying silica (from Acros: 0.035-0.070 mm, pore diameter ca. 6 nm) in dichloromethane (from Acros: >99.5% purity) and pouring it into a column. After packing the column, the solution from the rotavap (dissolved in dichloromethane) was poured over the column. The carbamate was eluted by running dichloromethane through the column. A sample was taken, and the purity measured on this sample was ~99.6%.

Example 11

The carbamate purified by the rotavap treatment in Example 10 needed to be re-dissolved in dichloromethane in order to run it through the silica column. Therefore it was logical to reverse the order of the rotovapping and silica column treatment. In addition, the synthesis step was done as in Example 1 but instead using dichloromethane as solvent.

Both rotovapping and silica column steps were carried out as in Examples 9 and 10 but in a reversed order. After the rotavap step, the purity of the carbamate was ~99.6%.

Discussion of Examples 8-11

Therefore it can be concluded that the silica column treatment followed by rotovapping gave the highest purity of the isolated carbamate product in the case of the preparation of the compound 1-methylsalicyl-N-diethylcarbamate.

Preparation of Other Carbamate Types

Example 12

In this example dipropyl amine was reacted with BMSC to form 1-methylsalicyl-N-dipropylcarbamate. 3.26 grams of bis-methylsalicyl carbonate and 1.00 grams of dipropylamine, corresponding to a 1:1 molar stoichiometric ratio (amine:BMSC), were dissolved in 10 milliliter of dichloromethane. The solution was stirred at room temperature under atmospheric conditions for 1 hour. The solution was analyzed by means of GC-FID. The results indicated that all of the dipropylamine has reacted to form methyl salicylate and the 1-methylsalicyl-N-dipropylcarbamate.

Example 13

In this example diisobutyl amine was reacted with BMSC to form 1-methylsalicyl-N-diisobutylcarbamate. 3.26 grams of bis-methylsalicyl carbonate and 1.277 grams of di-isobutylamine, corresponding to a 1:1 molar stoichiometric ratio (amine:BMSC), were dissolved in 10 milliliter of dichloromethane. The solution was stirred at room temperature under atmospheric conditions for 1 hour. The solution was analyzed by means of GC-FID. Results show that more than 50% of the di-isobutylamine had reacted to form methyl salicylate and the 1-methylsalicyl-N-diisobutylcarbamate. The solution was then left at room temperature and re-analyzed after a further three days. GC-FID analysis indicated that the di-isobutyl amine was essentially fully converted to 1-methylsalicyl-N-diisobutylcarbamate.

Discussion of examples 12 to 13 and their comparison with examples 1 and 4-6: These examples demonstrate that longer reaction times are needed to achieve high conversions when BMSC is reacted with amines that have a higher degree of substitution and/or are more sterically hindered.

Example 14

The following amine (benzylamine) is used in this example:

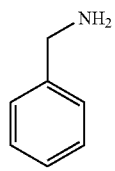

The reaction was carried out by dissolving 6 grams of BMSC and 0.9733 g of benzylamine (molar ratio 2:1) in 20 ml of dichloromethane. The synthesis was carried out in glassware that had been treated in an HCl solution (1M) for 24 hours in order to remove all traces of sodium ions that could be present on the glass surface and act as a catalyst in the reaction. The reaction was simply carried out by mixing the solution for 30 minutes at room temperature.

LC-MS analysis confirmed that the reaction mixture contained 1-methylsalicyl-N-benzylcarbamate.

Example 15

The procedure of example 14 was repeated except the molar ratio was changed to 1:1, therefore 6 grams of BMSC and 1.9465 g benzylamine were dissolved in 20 ml of dichloromethane.

LC-MS analysis confirmed that the reaction mixture contained the 1-methylsalicyl-N-benzylcarbamate.

Example 16 (Comparative)

The procedure of example 14 was repeated except that DMC was used. 6 g DMC and 7.1378 g of benzylamine were dissolved in 20 ml of dichloromethane.

LC-MS analysis showed that no carbamate was formed. A second analysis was done after 2 days of reaction, and it revealed that still no conversion was found for this example.

Example 17 (Comparative)

The procedure of Example 14 was repeated except that DPC was used. 6 g DPC and 3.0011 g of benzylamine were dissolved in 20 ml dichloromethane.

LC-MS analysis showed that no carbamate was formed. A second analysis was done after 2 days of reaction, and it revealed that still no conversion was found for this example. The results of examples 14-17 are displayed in the following Table.

| Example | Carbonate Source | Carbamate detected |
|---|---|---|
| 14 | BMSC | Yes |
| 15 | BMSC | Yes |
| 16 | DPC | ND |
| 17 | DMC | ND |

Preparation of Ureas

Example 18

Preparation of 1,3-dibutylurea was carried out by dissolving 6 grams of BMSC (source: Sabic Innovative Plastics NL) and 5.3 g of n-butylamine (Fisher, Product reference: 107802500, 99.5%) (molar stoichiometric ratio 1:4) in 18 ml of dichloromethane. The synthesis was carried out in glassware that had been treated in a HCl solution (1M) for 24 hours in order to remove all traces of sodium ions that could be present on the glass surface and act as a catalyst in the reaction. The reaction was simply carried out by mixing the solution for 30 minutes at room temperature. HPLC-MS characterization results validated that the urea had been formed.

Example 19 (Comparative)

The procedure of Example 18 was repeated except that diphenyl carbonate (DPC) was used as carbonate source.

Example 20 (Comparative)

The procedure of Example 18 was repeated except that dimethyl carbonate (DMC) was used as carbonate source.

The products of Examples 18-20 were evaluated for the yield of 1,3-dibutyl urea using calibrated HPLC. The results are summarized in Table 5.

TABLE 5

Reaction Yields for 1,3-dibutylurea

| Example | Carbonate Source | Yield (%) |
|---|---|---|
| 18 | BMSC | ~90 |
| 19 | DPC | ND |
| 20 | DMC | ND |

ND: Non detectable

As can be seen, the yield using BMSC in accordance with the invention was about 90%, while no product was detectable in either comparative example.

Example 21

6 grams of bis-methylsalicyl carbonate and 7.8 grams of benzylamine, corresponding to a 1:4 molar stoichiometric ratio, were dissolved in 20 milliliter of dichloromethane. The solution was stirred at room temperature under atmospheric conditions for 30 minutes. HPLC-MS characterization results validated that the 1,3-dibenzylurea had been formed.

Example 22 (Comparative)

The procedure of Example 17 was repeated except that DPC was used as carbonate source.

Example 23 (Comparative)

The procedure of Example 18 was repeated except that DMC was used as carbonate source.

The products of Examples 17-19 were evaluated for the yield of 1,3-dibenzylurea using calibrated HPLC. The results are summarized in Table 6.

TABLE 6

Reaction Yields for 1,3-dibenzylurea

| Example | Carbonate Source | Yield (%) |
|---|---|---|
| 21 | BMSC | ~90 |
| 22 | DPC | ND |
| 23 | DMC | ND |

ND: Non detectable

As can be seen, the yield using BMSC in accordance with the invention was about 90%, while no product was detectable in either of the comparative examples using DPC or DMC.

Example 24

To form the asymmetrical urea 1-benzyl-3-n-butylurea, 6 grams of bis-methylsalicyl carbonate and 1.9 gram of benzylamine, corresponding to a 1:1 molar stoichiometric ratio, were dissolved in 20 milliliter of dichloromethane. The solution was stirred at room temperature under atmospheric conditions for 90 minutes. In a second step 1.3 gram of butylamine, corresponding to a 1:1 molar ratio was added to the reaction mixture. The solution was again stirred at room temperature under atmospheric conditions for 90 minutes. HPLC-MS characterization results validated that the asymmetric urea had been formed.

Example 25

The following amine (aniline) was used in this example:

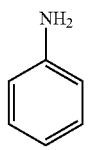

The synthesis was carried out in reaction tubes that had been treated in HCl (1M) solution for 24 hours in order to remove all traces of sodium ions that could be present on the glass surface and act as a catalyst in the reaction. The reaction was carried out by dissolving 1 g BMSC and 1.1277 g of aniline, corresponding to a 1:4 molar ratio (BMSC:aniline), in 6 ml of chloroform. As a catalyst 0.012 g of NaOH was added, this corresponds to a concentration of 10 mole % relative to that of the amine. Subsequently, the reaction mixture was stirred for 30 minutes at 61° C. (reflux).

LC-MS analysis of the solid, formed during the reaction, confirmed that the solid is 1,3-diphenylurea. The yield, calculated based on the methylsalicylate concentration, is 66%.

Example 26

The procedure of example 25 was repeated except that a reaction time of 60 minutes was used instead.

LC-MS analysis of the solid, formed during the reaction, confirmed that the solid was 1,3-diphenylurea. The yield, calculated based on the methylsalicylate concentration, is 81%.

Example 27 (Comparative)

The procedure of example 25 was repeated except that DPC was used. 1 g DPC and 1.7388 g of aniline were dissolved in 6 ml of chloroform. As a catalyst 0.075 g of NaOH was added.

HPLC analysis confirmed that the 1,3-diphenylurea is formed. The yield, based on total peak area, is 38%.

Example 28 (Comparative)

The procedure of example 25 was repeated except that DMC was used. 0.25 g DMC and 1.0399 g of aniline were dissolved in 6 ml of chloroform. As a catalyst 0.044 g of NaOH was added.

HPLC analysis confirms that no 1,3-diphenylurea was formed. The results of examples 25 to 28 are summarized in the following table. ND: not detectable.

| Example | Carbonate Source | Yield (%) |
|---|---|---|
| 25 | BMSC | ~66 |
| 26 | BMSC | ~81 |
| 27 | DPC | ~38 |
| 28 | DMC | ND |

Examples 25-28 show that BMSC has much better reactivity than DPC or DMC in the preparation of ureas. Only the BMSC-based urea was obtained with good conversion, in 30 minutes, compared to DMC and DPC. Also the urea examples show that BMSC has a higher reactivity and that a longer reaction time gave a higher yield.

Preparation of Cyclic Carbamates

Example 29

Figure 4:
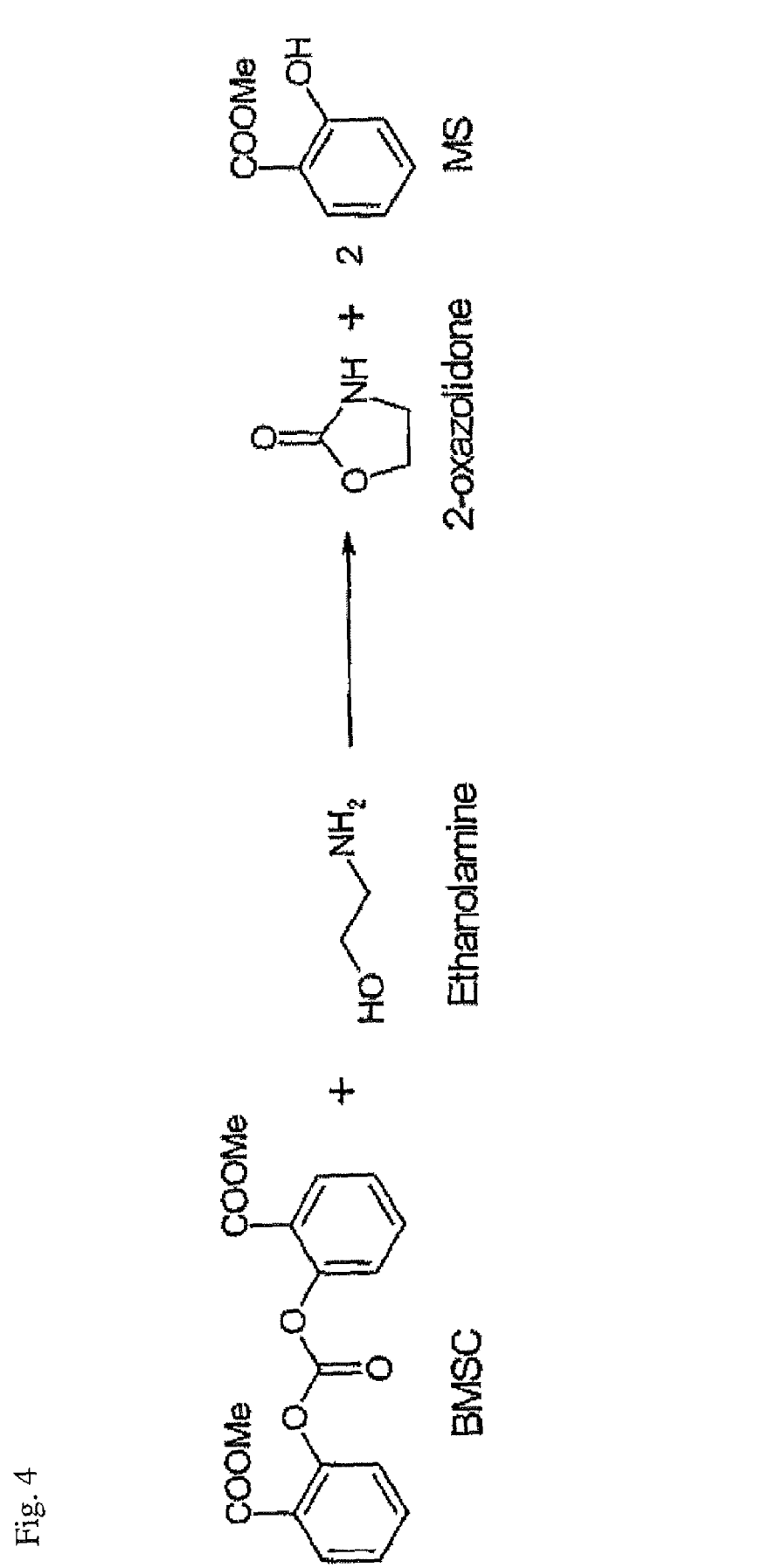
FIG. 4 shows the reaction of BMSC and ethanolamine to form 2-oxazolidine.

2-oxazolidone was prepared in accordance with the reaction in FIG. 4. The synthesis was carried out in 100 mL round bottom flasks that had been treated in a HCl solution (1M) for 24 hours in order to remove all traces of sodium ions that could be present on the glass surface and act as a catalyst in the reaction. The reaction was carried out by dissolving 6 g of BMSC and 1.1 g of ethanolamine in 18 ml of chloroform. Subsequently, the reaction mixture was stirred during 24 hours at room temperature. (Yield=12.8%).

Example 30

The procedure of Example 29 was repeated except that the reaction was carried out at reflux conditions (61° C.). (Yield=40.5%).

Example 31

The procedure of Example 29 was repeated except that a molar stoichiometric ratio triethylamine/BMSC equal to 0.1 was used as a catalyst. (Yield=40.8%).

Example 32

The procedure of Example 29 was repeated except that a molar stoichiometric ratio triethylamine/BMSC equal to 0.1 was used as a catalyst and the reaction was carried out at reflux conditions (61° C.). (Yield=78.5%).

Example 33

The synthesis of 2-oxazolidone was carried out in 100 mL round bottom flasks that had been treated in a HCl solution (1M) for 24 hours in order to remove all traces of sodium ions that could be present on the glass surface and act as a catalyst in the reaction. The reaction was performed in 2 steps. In a first step, 6 g of BMSC and 1.1 g of ethanolamine are dissolved in 18 ml of chloroform at room temperature and stirred for 60 minutes. In the second step the mixture is heated to 61° C. and triethylamine is added as catalyst (molar stoichiometric ratio triethylamine/BMSC equal to 0.1). The reaction mixture is left stirring during 240 minutes. (Yield=81.0%).

Example 34

The procedure of Example 33 was repeated except that in the first step, the reactants mixture is heated at 23° C. and stirred for 60 minutes. In the second step the mixture is heated to 61° C. and triethylamine is added as catalyst (molar stoichiometric ratio triethylamine/BMSC equal to 0.1). The reaction mixture is left stiffing during 240 minutes (Yield=84.0%).

Example 35

The procedure of Example 34 was repeated except that in the first step, the reactants mixture is heated at 61° C. and stirred for 15 minutes. In the second step the mixture is heated to 61° C. and triethylamine is added as catalyst (molar stoichiometric ratio triethylamine/BMSC equal to 0.3). The reaction mixture is left stirring during 85 minutes. (Yield=76.0%).

From the foregoing examples 29-35, it can be seen that increasing the temperature or adding a catalyst or both can substantially increase the yield of 2-oxazolidone. To further optimize the reactions conditions, an additional series of experiments were performed.

Example 36

The synthesis of 2-oxazolidone was carried out in 10 mL reactor tubes that had been previously treated in an HCl solution (1M) for 24 hours in order to remove all traces of sodium ions that could be present on the glass surface and act as a catalyst in the reaction. The reaction was carried out by dissolving 1 g of BMSC in 6 ml of chloroform. Then, 0.19 g of ethanolamine and a molar stoichiometric ratio triethylamine/BMSC equal to 0.5 were loaded. The reaction mixture was then left stirring during 100 minutes at reflux conditions (61° C.). (Yield=73.1%).

Example 37

The procedure of Example 36 was repeated except that a molar stoichiometric ratio triethylamine/BMSC equal to 1.0 was used as a catalyst. (Yield=71.8%).

Example 38

The procedure of Example 36 was repeated except that a molar stoichiometric ratio triethylamine/BMSC equal to 2.0 was used as a catalyst. (Yield=71.1%).

Example 39

The procedure of Example 36 was repeated except that a molar stoichiometric ratio triethylamine/BMSC equal to 0.3 was used as a catalyst and the reaction was carried out at reflux conditions (61° C.) during 90 minutes. (Yield=75.0%).

From these additional examples, it can be seen that the best yields are obtained with the stepwise procedure of Example 33. However, addition of catalyst substantially improves yield of the one step procedure and shortens the reaction time required (compare Example 29 and example 39). However, increasing the amount of catalyst from 0.1 to 1 mole catalyst/mole BMSC does not appear to improve reaction yield.

Example 40 (Comparative)

The procedure of Example 29 was repeated except that instead of using BMSC, 3.9 g of DPC were mixed with 1.1 g of ethanolamine in 18 ml of chloroform. A molar stoichiometric ratio triethylamine/DPC equal to 0.3 was used as a catalyst and the reaction was carried out at reflux conditions (61° C.) during 90 minutes. (Yield=9.0%).

Example 41 (Comparative)

The procedure of Example 29 was repeated except that instead of using BMSC, 1.65 g of DMC was mixed with 1.1 g of ethanolamine in 18 ml of chloroform. A molar stoichiometric ratio triethylamine/DMC equal to 0.3 was used as a catalyst and the reaction was carried out at reflux conditions (61° C.) during 90 minutes. (Yield=Below Detection Limits, BDL).

Discussion of (Comparative) Examples 40 and 41

A comparison of the (comparative) examples 40 and 41 using DPC and DMC, respectively, with example 29 using BMSC, shows that BMSC has much higher reactivity and conversion in the preparation of ureas under the mild reaction conditions used in these examples.

Example 42

After the synthesis steps described above, the 2-oxazolidinone was typically present in a mixture together with the methyl salicylate byproduct, the chloroform solvent, and some low levels of other by-products. In order to obtain the 2-oxazolidone compound in high purity (99.5%), the solvent was removed by rotavap vacuum distillation. As the boiling point of chloroform is 61° C., and that of methyl salicylate is 222° C., a solution of the product mixture in methyl salicylate was then obtained. The 2-oxazolidone was then crystallized by putting the obtained mixture in an ice bath and then filtered and washed with cold dimethyl ether in the same filtration system. The remaining dimethyl ether was completely removed in a vacuum oven. After this purification process the purity of the 2-oxazolidone synthesized was increased to 99.5%.

Table 7 tabulates a summary of the yields observed in Examples 29-42.

TABLE 7

| Example | Reaction Steps | Carbonate | Temp. (° C.) | Time (minutes) | Catalyst (mol ratio/carbonate) | Yield (%) |
|---|---|---|---|---|---|---|
| 29 | 1 | BMSC | RT | 1440 | 0 | 12.8 |
| 30 | 1 | BMSC | 61 | 1440 | 0 | 40.5 |
| 31 | 1 | BMSC | RT | 1440 | 0.1 | 40.8 |
| 32 | 1 | BMSC | 61 | 1440 | 0.1 | 78.5 |
| 33 | 2 | BMSC | 0 and 61 | 60 and 240 | 0.1 | 81.0 |
| 34 | 2 | BMSC | 23 and 61 | 60 and 240 | 0.1 | 84.0 |
| 35 | 2 | BMSC | 61 and 61 | 15 and 85 | 0.3 | 76.0 |
| 36 | 1 | BMSC | 61 | 100 | 0.5 | 73.1 |
| 37 | 1 | BMSC | 61 | 100 | 1.0 | 71.8 |
| 38 | 1 | BMSC | 61 | 100 | 2.0 | 71.1 |
| 39 | 1 | BMSC | 61 | 90 | 0.3 | 75.0 |
| 40 | 1 | DPC | 61 | 90 | 0.3 | 9.0 |
| 41 | 1 | DMC | 61 | 90 | 0.3 | BDL |
| 42 | Purified material: 99.5% purity. | | | | | |

BDL = Below Detection Limits.
DPC = Diphenyl carbonate.
DMC = Dimethyl carbonate.

Example 43

Figure 10:
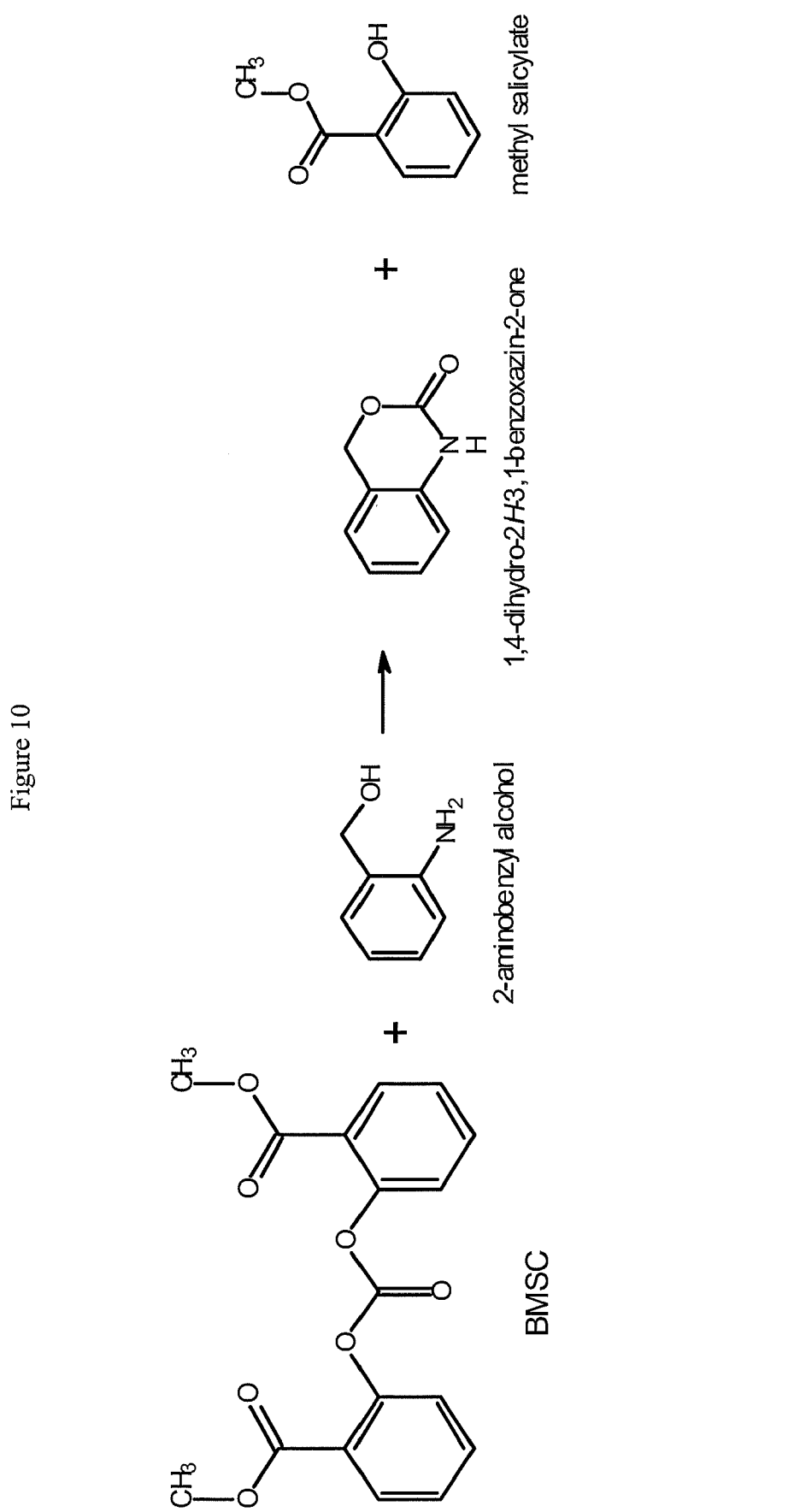
FIG. 10 shows a cyclic carbamate formation reaction in accordance with the example section.

The mechanism and reaction scheme for the synthesis of 1,4-dihydro-2H-3,1-benzoxazin-2-one is shown in FIG. 10. The synthesis was carried out under the same reaction conditions and setup as described in Example 3 (30 min at RT), except that 1.982 grams of BMSC were dissolved in 10 ml of chloroform in a round bottom flask while stirring. Then 0.74 grams of 2-aminobenzyl alcohol were added followed by 0.19 mL of NaOH (0.5 mol %). The formation of the 1,4-dihydro-2H-3,1-benzoxazin-2-one was confirmed by a combination of GCFID and GC-MS and/or LC-MS methods.

Example 44

The mechanism and reaction scheme for the synthesis of 2(3H)-Benzoxazolone is shown in FIG. 11. The synthesis was carried out under the same reaction conditions and setup as described in Example 3 (30 min. at RT), except that 1.982 grams of BMSC were dissolved in 10 ml of chloroform in a round bottom flask while stirring. Then 0.65 grams of 2-aminophenol were added followed by 0.19 mL of NaOH (0.5 mol %). The formation of the 2(3H)-Benzoxazolone was confirmed by a combination of GCFID and GC-MS and/or LC-MS methods.

Preparation of Isocyanates

Example 45

Figure 5:
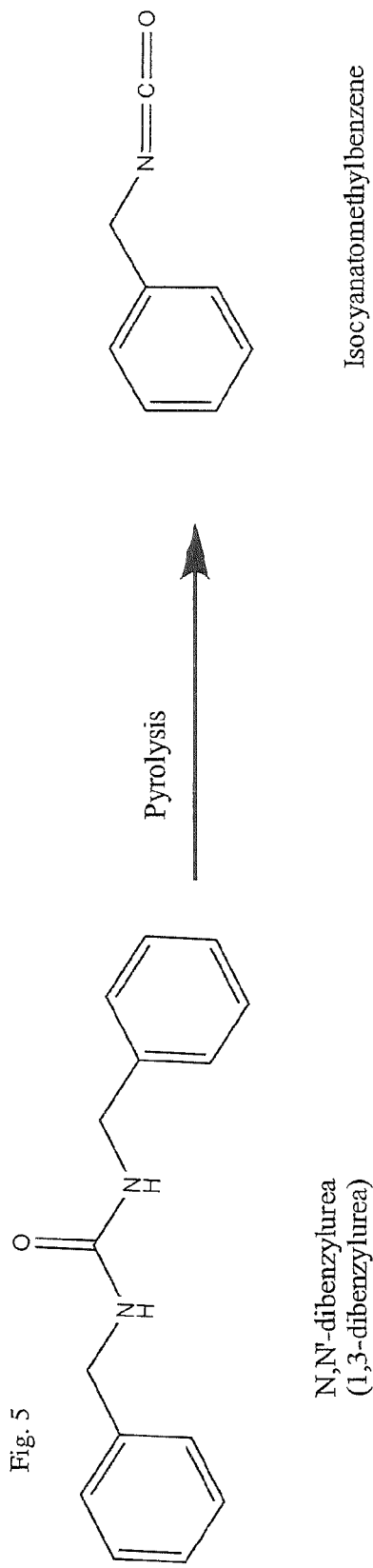
FIG. 5. shows the pyrolysis of 1,3-dibenzylurea to form (isocyanatomethyl)benzene.

(Isocyanatomethyl)benzene was prepared by pyrolysis of 1,3-dibenzylurea prepared in Example 17 as shown in FIG. 5. Because of environmental, health and safety concerns the reaction to perform the isocyanate had to be done in a closed system and using as low amounts as possible. Therefore the thermal pyrolysis reaction was carried out in a TDS-GC-MS in order to form the isocyanate and identify it as it is formed by running it through the mass spectrometer unit. The predominant product detected was the desired (isocyanatomethyl)benzene, although smaller amounts of benzonitrile, benzyleamine and N-(phenylmethylene)-benzenemethanamine were also detected, together with a small amount of the unreacted starting material. The pyrolysis in this specific example was carried out at the non-limiting temperature of 350° C. Milder reaction temperatures for this step may, of course, be used also.

Example 46

Figure 6:
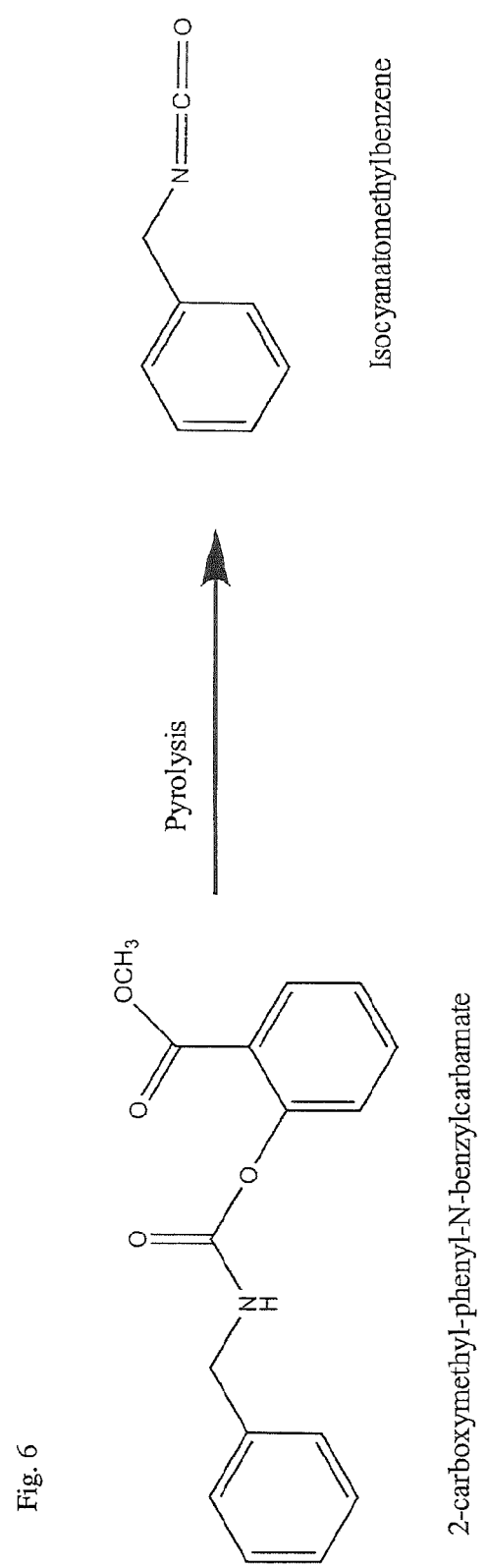
FIG. 6 shows the pyrolysis of a carbamate to form (isocyanatomethyl)benzene.

6 grams of bis-methylsalicyl carbonate and 1.97 grams of benzylamine, corresponding to a 1:1 molar ratio, were dissolved in 20 milliliter of dichloromethane. The solution was stirred at room temperature under atmospheric conditions for 30 minutes to form 2-methoxyphenyl benzylcarbamate. (Isocyanatomethyl)benzene was prepared by pyrolysis of this carbamate as shown in FIG. 6 using the same procedure as in Example 45. The desired isocyanate was observed to be formed.

Preparation of Cyclic Ureas

Example 47

The mechanism and reaction scheme for the synthesis of imidazolidin-2-one is shown in FIG. 12. The synthesis was carried out under the same reaction conditions and setup as described in Example 3 (30 min at RT), except that 1.982 grams of BMSC were dissolved in 10 mL of chloroform in a round bottom flask while stirring. Then 41 mL of ethylenediamine was added followed by 0.19 mL of NaOH (0.5 mol %). The formation of the imidazolidin-2-one was confirmed by a combination of GCFID, GC-MS and LC-MS methods.

Literature Comparison with Phosgene Reactions

From the examples above, it can be seen that it is possible to prepare a variety of carbamate, urea, and isocyanate compounds from ortho-ester-substituted carbonates such as BMSC. The reactions of amines with BMSC go essentially to full conversion even at relatively low reaction temperatures, e.g. room temperature. Depending on the reaction stoichiometry (molar ratio amine:carbonate) chosen, one may either prepare carbamates by using a stoichiometry of 1:1 or less, or ureas may be prepared by using a stoichiometry of greater than 1:1, preferably greater than or equal to 2:1.

A comparison of the reactivity of BMSC with a non-activated carbonate like DPC or DMC indicate that the non-activated carbonates give little or no conversion at similar reaction conditions used in the preparation of carbamates or ureas at high conversion from BMSC. Comparisons of some of this experimental data from the examples and from the literature are summarized in Table 8 below.

We have also compared specific examples made using the method of the invention with examples in the literature of making compounds using triphosgene or other alkyl carbonates. This comparison is also in Table 8.

TABLE 8

| | Carbonate | Amine | ratio carbonate/amine | Temp. | Time | Catalyst | Synthetized compound | yield (%) | Source |
|---|---|---|---|---|---|---|---|---|---|
| 1 | ethylene carbonate | n-butyl amine | 1/2 | 100° C. | 1 h | CaO | 1,3-dibuyl urea | 49 | Fujita et al., 2004 [5] |
| 2 | ethylene carbonate | n-butyl amine | 1/2 | 100° C | 3 h | CaO | 1,3-dibutyl urea | 78 | Fujita et al., 2004 [5] |
| 3 | triphosgene | primary aromatic amine | 1/2 | 50° C. | 8 h | no, but controled pH | urea | 93.5 | Peng et al., 1996 [8] |
| 4 | BMSC | n-butyl amine | 1/4 | room T | 30 min | no | 1,3-dibuyl urea | 91 | experimental data |
| 5 | DMC | n-butyl amine | 1/4 | room T | 30 min | no | 1,3-dibuyl urea | 0 | experimental data |
| 6 | DPC | n-butyl amine | 1/4 | room T | 30 min | no | 1,3-dibuyl urea | 0 | experimental data |
| 7 | dimethyl carbonate | n-butyl amine | 5/1 | 80° C. | 8 h | Yb(OTf)3 | 1-methyl-N-butyl carbamate | 93 | Curini et al., 2002 [3] |
| 8 | dimethyl carbonate | n-octyl amine | 1/2 | room T | 7 days | Al2O3 | 1-methyl-N-octyl carbamate | 95 | Vauthey et al., 2000 [4] |

Full source for rows 1 & 2: Fujita S-I et al., Synthesis of 1,3-dialkylurea from ethylene carbonate and amine using calcium oxide, Journal of molecular catalysis-A: chemical, 230, 43-48, 2005.
Full source for row 3: Peng et al., N,N'-Phosgenation with Triphosgene in the Synthesis of Direct Dyes containing the Ureylene Group, Dyes and Pigments, Volome 32. No. 4, 193-198, 1996
Full source for row 7: Curini M. et al., Carbamate synthesis from amines and dimethyl carbonate under ytterbium triflate catalysis, Tetrahedron Letters, Volume 43, Issue 28, 8 Jul. 2002, Pages 4895-4897.
Full source for row 8: Vauthey I. et al., An environmentally benign access to carbamate and ureas. Tetrahedron Letters, Volume 41, Issue 33, 2000, Pages 6347-6350.
The data from the above table demonstrate that ureas can be made from BMSC at ambient temperatures in short reaction times and in high yields; whereas the comparable ureas or even carbamates require the use of catalysts and either long reaction times and/or elevated reaction temperatures when employing the methods of the art.

The invention claimed is:

1. A method of making a compound of the formula:

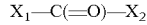

$X_1$—C(=O)—$X_2$ wherein $X_1$ is $NR_1R_2$ and $X_2$ is $NR_3R_4$ or $OR_5$, and wherein $R_1$, $R_2$, and $R_3$ and $R_4$, if present, are each independently selected from the group consisting of hydrogen, optionally-substituted linear or branched alkyl, a heteroatom-containing alkyl, alkene, cycloalkyl, cycloalkenyl, aryl, heteroatom-containing aryl, heteroatom-containing aralkyl, and aralkyl groups, or $R_1$ and $R_2$ in combination are a carbon atom double bonded to the nitrogen of $X_1$ or $R_3$ and $R_4$ in combination are a carbon atom double bonded to the nitrogen of $X_2$ or the N of $X_1$ or $X_2$ may be the nitrogen of a ring system, and $R_5$, if present, is selected from the group consisting of optionally-substituted linear or branched alkyl, a heteroatom-containing alkyl, aryl, heteroatom-containing aralkyl, and aralkyl groups, or $R_1$ or $R_2$ in combination with $R_3$, $R_4$, or $R_5$ form a five or six-member ring, said method comprising reacting $HNR_1R_2$, and $HNR_3R_4$ or $HOR_5$ with an ester-substituted diaryl carbonate to form the compound.

2. The method of claim 1, wherein the ester-substituted diaryl carbonate is bismethylsalicylcarbonate (BMSC).

3. The method of claim 1, wherein $X_2$ is $NR_3R_4$, whereby the compound formed is a urea.

4. The method of claim 3, said method comprising reacting at least two moles of one or more primary or secondary amines or one mole diamine with an ester-substituted diaryl carbonate to form the urea.

5. The method of claim 3, wherein $R_1$ or $R_2$ in combination with $R_3$ or $R_4$ forms a five or six-member ring.

6. The method of claim 1, wherein $X_2$ is $OR_5$, whereby the compound formed is a carbamate.

7. The method of claim 6, said method comprising combining a primary or secondary amine with an ester-substituted diaryl carbonate to form a reaction mixture, and allowing the reactions mixture to react to form the carbamate.

8. The method of claim 7, where the reaction mixture further comprises an alcohol.

9. The method of claim 6, wherein $R_1$ or $R_2$ in combination with $R_5$ forms a five or six-member ring.

10. The method of claim 1, wherein the reaction is performed at a temperature of less than 120° C.

11. The method of claim 10, wherein the reaction is performed at a temperature of less than 60° C.

12. The method of claim 1, wherein the reaction is performed for a period of 24 hours or less.

13. The method of claim 12, wherein the reaction is performed for a period of 4 hours or less.

14. The method of claim 13, wherein the reaction is performed for a period of 30 minutes to one hour.

15. The method of claim 1, wherein the reaction is performed in the presence of a catalyst.

16. The method of claim 15, wherein the catalyst is present in an amount of 0.1 to 1 mole catalyst per mole of ester-substituted diaryl carbonate.

17. The method of claim 1, wherein the reaction is performed in the absence of any catalyst.

18. A method for forming isocyanates, comprising forming a compound in accordance with claim 1, and pyrolyzing the compound to form an isocyanate.

* * * * *